US007429261B2

(12) United States Patent
Kunis et al.

(10) Patent No.: US 7,429,261 B2
(45) Date of Patent: Sep. 30, 2008

(54) ATRIAL ABLATION CATHETER AND METHOD OF USE

(75) Inventors: Christopher G. Kunis, San Diego, CA (US); Thomas M. Castellano, Tomacula, CA (US); Marshall L. Sherman, Cardiff by Sea, CA (US); Randell L. Werneth, San Diego, CA (US)

(73) Assignee: Ablation Frontiers, Inc., Carlsbad, CA (US)

( * ) Notice: Subject to any disclaimer, the term of this patent is extended or adjusted under 35 U.S.C. 154(b) by 0 days.

(21) Appl. No.: 10/997,172

(22) Filed: Nov. 24, 2004

(65) Prior Publication Data

US 2006/0111700 A1 May 25, 2006

(51) Int. Cl.
*A61B 18/18* (2006.01)
*A61N 1/00* (2006.01)
(52) U.S. Cl. .................. 606/41; 607/122; 606/47
(58) Field of Classification Search .................. 606/41, 606/47–50; 607/116, 122, 101, 102
See application file for complete search history.

(56) References Cited

U.S. PATENT DOCUMENTS

| 3,516,412 | A | | 6/1970 | Ackerman |
| 4,411,266 | A | | 10/1983 | Cosman |
| 4,432,377 | A | | 2/1984 | Dickhudt |
| 4,660,571 | A | | 4/1987 | Hess et al. |
| 4,785,815 | A | | 11/1988 | Cohen |
| 4,860,769 | A | | 8/1989 | Fogarty |
| 4,869,248 | A | | 9/1989 | Narula |
| 4,882,777 | A | | 11/1989 | Narula |
| 4,896,671 | A | | 1/1990 | Cunningham et al. |
| 4,920,980 | A | | 5/1990 | Jackowski |
| 4,966,597 | A | | 10/1990 | Cosman |
| 5,010,894 | A | | 4/1991 | Edhag ...................... 128/785 |
| 5,016,808 | A | | 5/1991 | Heil |
| 5,083,565 | A | | 1/1992 | Parius |
| 5,156,151 | A | | 10/1992 | Imran |
| 5,184,621 | A | * | 2/1993 | Vogel et al. ................ 600/381 |
| 5,228,442 | A | | 7/1993 | Imran |
| 5,239,999 | A | | 8/1993 | Imran et al. |
| 5,255,679 | A | | 10/1993 | Imran |
| 5,279,299 | A | | 1/1994 | Imran et al. |
| 5,281,218 | A | | 1/1994 | Imran |
| 5,313,943 | A | * | 5/1994 | Houser et al. ............... 600/374 |
| 5,324,284 | A | | 6/1994 | Imran |
| 5,327,889 | A | | 7/1994 | Imran et al. |
| 5,330,466 | A | | 7/1994 | Imran |
| 5,342,295 | A | | 8/1994 | Imran |
| 5,345,936 | A | | 9/1994 | Pomeranz et al. |

(Continued)

FOREIGN PATENT DOCUMENTS

AU 5200671 10/2005

(Continued)

*Primary Examiner*—Michael Peffley
(74) *Attorney, Agent, or Firm*—Shay Glenn LLP (57) ABSTRACT

An atrial ablation catheter and methods for its use. The endocardial catheter includes an electrode array particularly adapted to locate and ablate foci of arrhythmia which are required for sustained atrial fibrillation is provided. The array is easily deployed and retracted from the catheter, and presents a distally oriented electrode array that can be pressed against the wall of the atrium.

21 Claims, 6 Drawing Sheets

U.S. PATENT DOCUMENTS

| | | |
|---|---|---|
| 5,383,917 A | 1/1995 | Desai et al. |
| 5,391,147 A | 2/1995 | Imran et al. |
| 5,397,339 A | 3/1995 | Desai et al. |
| 5,400,783 A | 3/1995 | Pomeranz et al. |
| 5,404,638 A | 4/1995 | Imran |
| 5,406,946 A | 4/1995 | Imran |
| 5,445,148 A | 8/1995 | Jaraczewski et al. |
| 5,462,545 A | 10/1995 | Wang |
| 5,465,717 A | 11/1995 | Imran et al. |
| 5,487,757 A | 1/1996 | Truckai et al. |
| 5,492,119 A | 2/1996 | Abrams |
| 5,507,802 A | 4/1996 | Imran |
| 5,509,411 A | 4/1996 | Littmann et al. |
| 5,527,279 A | 6/1996 | Imran |
| 5,533,967 A | 7/1996 | Imran |
| 5,545,193 A | 8/1996 | Fleischman et al. |
| 5,545,200 A | 8/1996 | West |
| 5,558,073 A | 9/1996 | Pomeranz et al. |
| 5,575,810 A | 11/1996 | Swanson et al. |
| 5,578,007 A | 11/1996 | Imran |
| 5,582,609 A | 12/1996 | Swanson et al. |
| 5,588,964 A | 12/1996 | Imran et al. |
| 5,595,183 A | 1/1997 | Swanson et al. |
| 5,598,848 A | 2/1997 | Swanson et al. |
| 5,607,462 A | 3/1997 | Imran |
| 5,637,090 A | 6/1997 | McGee et al. |
| 5,645,064 A | 7/1997 | Littmann et al. |
| 5,656,029 A | 8/1997 | Imran et al. |
| 5,666,970 A | 9/1997 | Smith |
| 5,680,860 A | 10/1997 | Imran |
| 5,682,885 A | 11/1997 | Littmann et al. |
| 5,687,723 A | 11/1997 | Avital |
| 5,693,078 A | 12/1997 | Desai et al. |
| 5,697,928 A | 12/1997 | Walcott et al. |
| 5,699,796 A | 12/1997 | Littmann et al. |
| 5,706,809 A | 1/1998 | Littmann et al. |
| 5,711,298 A | 1/1998 | Littman et al. |
| 5,741,320 A | 4/1998 | Thornton et al. |
| 5,782,760 A | 7/1998 | Schaer |
| 5,782,828 A | 7/1998 | Chen et al. |
| 5,800,482 A | 9/1998 | Pomeranz et al. |
| 5,827,272 A | 10/1998 | Breining et al. |
| 5,837,001 A | 11/1998 | Mackey |
| 5,860,920 A | 1/1999 | McGee et al. |
| 5,863,291 A | 1/1999 | Schaer |
| 5,871,523 A | 2/1999 | Fleischman et al. |
| 5,876,399 A | 3/1999 | Chia et al. |
| 5,882,333 A | 3/1999 | Schaer et al. |
| 5,885,278 A | 3/1999 | Fleischman |
| 5,891,027 A | 4/1999 | Tu et al. |
| 5,891,135 A | 4/1999 | Jackson |
| 5,891,137 A | 4/1999 | Chia et al. |
| 5,893,847 A | 4/1999 | Kordis |
| 5,895,355 A | 4/1999 | Schaer |
| 5,895,417 A | 4/1999 | Pomeranz et al. |
| 5,897,554 A | 4/1999 | Chia et al. |
| 5,904,680 A | 5/1999 | Kordis |
| 5,906,605 A | 5/1999 | Coxum |
| 5,910,129 A | 6/1999 | Koblish et al. |
| 5,911,720 A | 6/1999 | Bourne et al. ................ 606/41 |
| 5,916,214 A | 6/1999 | Cosio et al. |
| 5,928,191 A | 7/1999 | Houser et al. |
| 5,931,835 A | 8/1999 | Mackey |
| 5,935,063 A | 8/1999 | Nguyen |
| 5,938,694 A | 8/1999 | Jaraczewski et al. |
| 5,951,471 A | 9/1999 | de la Rama et al. |
| 5,967,978 A | 10/1999 | Littmann et al. |
| 5,992,418 A | 11/1999 | de la Rama et al. |
| 5,997,532 A | 12/1999 | McLaughlin et al. |
| 6,001,093 A | 12/1999 | Swanson et al. |
| 6,001,095 A | 12/1999 | de la Rama et al. |
| 6,002,956 A | 12/1999 | Schaer |
| 6,029,091 A | 2/2000 | de la Rama et al. |
| 6,032,674 A * | 3/2000 | Eggers et al. ................ 128/898 |
| 6,042,580 A | 3/2000 | Simpson |
| 6,048,329 A | 4/2000 | Thompson et al. |
| 6,049,737 A | 4/2000 | Simpson et al. |
| 6,053,937 A | 4/2000 | Edwards et al. ............. 607/104 |
| 6,056,744 A * | 5/2000 | Edwards ...................... 606/41 |
| 6,059,778 A | 5/2000 | Sherman et al. |
| 6,063,077 A | 5/2000 | Schaer |
| 6,063,082 A | 5/2000 | DeVore et al. ................ 606/45 |
| 6,068,629 A | 5/2000 | Haissaguerre |
| 6,070,094 A | 5/2000 | Swanson et al. |
| 6,071,274 A | 6/2000 | Thompson et al. |
| 6,071,279 A | 6/2000 | Whayne et al. |
| 6,071,282 A * | 6/2000 | Fleischman .................. 606/41 |
| 6,074,351 A | 6/2000 | Houser et al. |
| 6,086,581 A | 7/2000 | Reynolds et al. |
| 6,088,610 A | 7/2000 | Littmann et al. |
| 6,096,036 A | 8/2000 | Bowe et al. |
| 6,099,524 A | 8/2000 | Lipson |
| 6,106,522 A | 8/2000 | Fleischman et al. |
| 6,119,041 A | 9/2000 | Pomeranz et al. |
| 6,129,724 A | 10/2000 | Fleischman et al. |
| 6,141,576 A | 10/2000 | Littmann et al. |
| 6,146,379 A | 11/2000 | Fleischman et al. |
| 6,171,306 B1 | 1/2001 | Swanson et al. |
| 6,200,314 B1 | 3/2001 | Sherman et al. |
| 6,214,002 B1 | 4/2001 | Fleischman et al. |
| 6,216,043 B1 | 4/2001 | Swanson et al. |
| 6,216,044 B1 | 4/2001 | Kordis |
| 6,238,390 B1 | 5/2001 | Tu et al. |
| 6,241,666 B1 | 6/2001 | Pomeranz et al. |
| 6,241,724 B1 | 6/2001 | Fleischman et al. |
| 6,241,726 B1 | 6/2001 | Chia |
| 6,241,754 B1 | 6/2001 | Swanson et al. |
| 6,245,067 B1 | 6/2001 | Tu et al. |
| 6,251,107 B1 | 6/2001 | Schaer et al. |
| 6,256,540 B1 | 7/2001 | Panescu et al. |
| 6,267,746 B1 | 7/2001 | Bumbalough |
| 6,290,697 B1 | 9/2001 | Tu et al. |
| 6,302,880 B1 | 10/2001 | Schaer |
| 6,309,385 B1 | 10/2001 | Simpson |
| 6,319,251 B1 * | 11/2001 | Tu et al. ...................... 606/41 |
| 6,332,880 B1 | 12/2001 | Yang et al. |
| 6,332,881 B1 | 12/2001 | Carner et al. |
| 6,346,104 B2 | 2/2002 | Daly et al. |
| 6,353,751 B1 | 3/2002 | Swanson et al. |
| 6,360,128 B2 | 3/2002 | Kordis et al. |
| 6,371,955 B1 | 4/2002 | Fuimaono et al. |
| 6,379,352 B1 | 4/2002 | Reynolds et al. |
| 6,428,536 B2 | 8/2002 | Panescu et al. |
| 6,447,506 B1 | 9/2002 | Swanson et al. |
| 6,454,758 B1 | 9/2002 | Thompson et al. |
| 6,456,864 B1 | 9/2002 | Swanson et al. |
| 6,460,545 B2 | 10/2002 | Kordis |
| 6,471,699 B1 | 10/2002 | Fleischman et al. |
| 6,475,213 B1 | 11/2002 | Whayne et al. |
| 6,475,214 B1 | 11/2002 | Moaddeb |
| 6,477,396 B1 | 11/2002 | Mest |
| 6,488,678 B2 | 12/2002 | Sherman et al. |
| 6,500,172 B1 | 12/2002 | Panescu et al. |
| 6,514,246 B1 | 2/2003 | Swanson et al. |
| 6,544,262 B2 | 4/2003 | Fleishman |
| 6,554,794 B1 | 4/2003 | Mueller et al. |
| 6,558,378 B2 | 5/2003 | Sherman et al. |
| 6,572,612 B2 | 6/2003 | Stewart et al. |
| 6,574,492 B1 | 6/2003 | Ben-Haim et al. |
| 6,607,505 B1 | 8/2003 | Thompson et al. |
| 6,607,520 B2 | 8/2003 | Keane |
| 6,628,976 B1 | 9/2003 | Fuimaono et al. |
| 6,632,223 B1 | 10/2003 | Keane |
| 6,640,120 B1 | 10/2003 | Swanson et al. |

| Patent No. | Date | Inventor |
|---|---|---|
| 6,658,279 B2 | 12/2003 | Swanson et al. |
| 6,669,693 B2 | 12/2003 | Friedman |
| 6,702,811 B2 | 3/2004 | Stewart |
| 6,746,446 B1 | 6/2004 | Hill et al. |
| 6,805,131 B2 | 10/2004 | Kordis |
| 6,813,520 B2 | 11/2004 | Truckai et al. |
| 6,814,732 B2 | 11/2004 | Schaer |
| 6,830,576 B2 | 12/2004 | Fleischman et al. |
| 6,893,439 B2 | 5/2005 | Fleischman |
| 6,952,615 B2 * | 10/2005 | Satake .................. 607/102 |
| 6,961,602 B2 | 11/2005 | Fuimaono et al. |
| 6,966,908 B2 | 11/2005 | Maguire et al. |
| 6,972,016 B2 | 12/2005 | Hill et al. |
| 7,025,766 B2 | 4/2006 | Whayne et al. |
| 7,029,471 B2 | 4/2006 | Thompson et al. |
| 7,047,068 B2 | 5/2006 | Haissaguerre |
| 7,048,734 B1 | 5/2006 | Fleischman et al. |
| 7,099,172 B2 | 8/2006 | Fuimaono et al. |
| 7,115,122 B1 | 10/2006 | Swanson et al. |
| 7,151,964 B2 | 12/2006 | Desai |
| 7,155,270 B2 | 12/2006 | Solis et al. |
| 7,163,537 B2 | 1/2007 | Lee et al. |
| 2001/0018608 A1 | 8/2001 | Panescu et al. |
| 2001/0020166 A1 | 9/2001 | Daly et al. |
| 2001/0039418 A1 | 11/2001 | Schaer |
| 2002/0065465 A1 | 5/2002 | Panescu et al. |
| 2002/0161422 A1 | 10/2002 | Swanson et al. |
| 2002/0165532 A1 | 11/2002 | Hill et al. |
| 2002/0198522 A1 | 12/2002 | Kordis |
| 2003/0093069 A1 | 5/2003 | Panescu et al. |
| 2003/0204186 A1 | 10/2003 | Geistert et al. |
| 2004/0116921 A1 | 6/2004 | Sherman |
| 2005/0015084 A1 | 1/2005 | Hill et al. |
| 2005/0065512 A1 | 3/2005 | Schaer |
| 2005/0177146 A1 | 8/2005 | Sherman |
| 2006/0089637 A1 | 4/2006 | Sherman et al. |
| 2006/0106375 A1 | 5/2006 | Sherman |
| 2006/0111700 A1 | 5/2006 | Sherman |
| 2006/0111708 A1 | 5/2006 | Vanney et al. |
| 2006/0189975 A1 | 8/2006 | Whayne et al. |
| 2006/0206109 A1 | 9/2006 | Swanson |
| 2006/0241366 A1 | 10/2006 | Falwell et al. |
| 2007/0027448 A1 | 2/2007 | Paul |

FOREIGN PATENT DOCUMENTS

| | | |
|---|---|---|
| CA | 2276755 C | 5/2006 |
| CA | 2251041 C | 6/2006 |
| EP | 0428812 B1 | 10/1997 |
| EP | 0598742 B1 | 8/1999 |
| EP | 0957794 B1 | 11/1999 |
| EP | 0879016 B1 | 10/2003 |
| EP | 1384445 B1 | 2/2006 |
| EP | 1011437 B1 | 5/2006 |
| EP | 1207798 B1 | 6/2006 |
| EP | 1321166 B1 | 7/2006 |
| EP | 1690564 A1 | 8/2006 |
| EP | 0828451 B1 | 9/2006 |
| EP | 1014874 B1 | 12/2006 |
| EP | 1455667 B1 | 1/2007 |
| WO | WO 96/34570 | 11/1986 |
| WO | WO 90/06079 | 6/1990 |
| WO | WO 94/12098 | 6/1994 |
| WO | WO 96/10961 | 4/1996 |
| WO | WO 98/19611 | 5/1996 |
| WO | WO 96/34559 | 11/1996 |
| WO | WO 96/34560 | 11/1996 |
| WO | WO 96/34653 | 11/1996 |
| WO | WO 97/17904 | 5/1997 |
| WO | WO 97/25917 | 7/1997 |
| WO | WO 97/25919 | 7/1997 |
| WO | WO 9732525 | 9/1997 |
| WO | WO 97/36541 | 10/1997 |
| WO | WO 97/40760 | 11/1997 |
| WO | WO 97/42996 | 11/1997 |
| WO | WO 98/18520 | 5/1998 |
| WO | WO 98/26724 | 6/1998 |
| WO | WO 99/56649 | 11/1999 |
| WO | WO 03/089997 | 10/2003 |
| WO | WO 2005/065562 | 7/2005 |
| WO | WO 2005/065563 | 7/2005 |
| WO | WO 2005/104972 | 11/2005 |
| WO | WO 2006/017517 | 2/2006 |
| WO | WO 2006/044794 | 4/2006 |
| WO | WO 2006/049970 | 5/2006 |
| WO | WO 2006/052651 | 5/2006 |
| WO | WO 2006/052905 | 5/2006 |
| WO | WO 2007/024785 | 3/2007 |
| WO | WO 2007/016123 | 2/2008 |

* cited by examiner

Fig. 1

Patch Electrode

Control System

Fig. 14 ance of death in the United States.

ATRIAL ABLATION CATHETER AND METHOD OF USE

FIELD OF THE INVENTIONS

The inventions described below relate the field of atrial ablation.

BACKGROUND OF THE INVENTIONS

Atrial fibrillation is a form of arrhythmia, or irregular heartbeat, in which the atria (the two small upper chambers of the heart) quiver instead of beating effectively. While there are a number of variations of atrial fibrillation with different causes, they all involve irregularities in the transmission of electrical impulses through the heart. As a result of abnormalities in the heart's electrical impulses, the heart is not able to pump the blood out properly, and it may pool and clot. If a blood clot moves to an artery in the brain, AF can lead to stroke. AF is also associated with increased risks of congestive heart failure and cardiomyopathy. These risks warrant medical attention for patients with AF even if the symptoms are mild. Atrial fibrillation is the most common sustained heart rhythm disorder and increases the risk for heart disease and stroke, both leading causes of death in the United States. Over 2 million adults in the United States have been diagnosed with atrial fibrillation.

Various ablation techniques have been proposed to treat atrial fibrillation, including the Cox-Maze procedure, linear ablation of various regions of the atrium, and circumferential pulmonary vein ablation. Each of these techniques has its various drawbacks. The Cox-Maze procedure and linear ablation procedures are tedious and time-consuming, taking up to several hours to accomplish endocardially. Circumferential ablation is proving to lead to rapid stenosis and occlusion of the pulmonary veins. Thus, improved atrial ablation techniques are sorely needed.

SUMMARY

The devices and methods described below provide for a simplified approach to the treatment of atrial fibrillation with substantially improved efficacy & outcomes in patients with paroxysmal or persistent atrial fibrillation. An endocardial catheter with an electrode array particularly adapted to locate and ablate foci of arrhythmia which are required for sustained atrial fibrillation is provided. The array is easily deployed and retracted from the catheter, and presents a distally oriented electrode array that can be pressed flat against the wall of the atrium. A control system comprising an ECG analyzer and a RF power supply operates to analyze electrical signals obtained from the electrode array, determine if an arrythmogenic focus is present in the area covered by the array, and supply RF power to appropriate electrodes to ablate the focus.

DETAILED DESCRIPTION OF THE INVENTIONS

Figure 1:
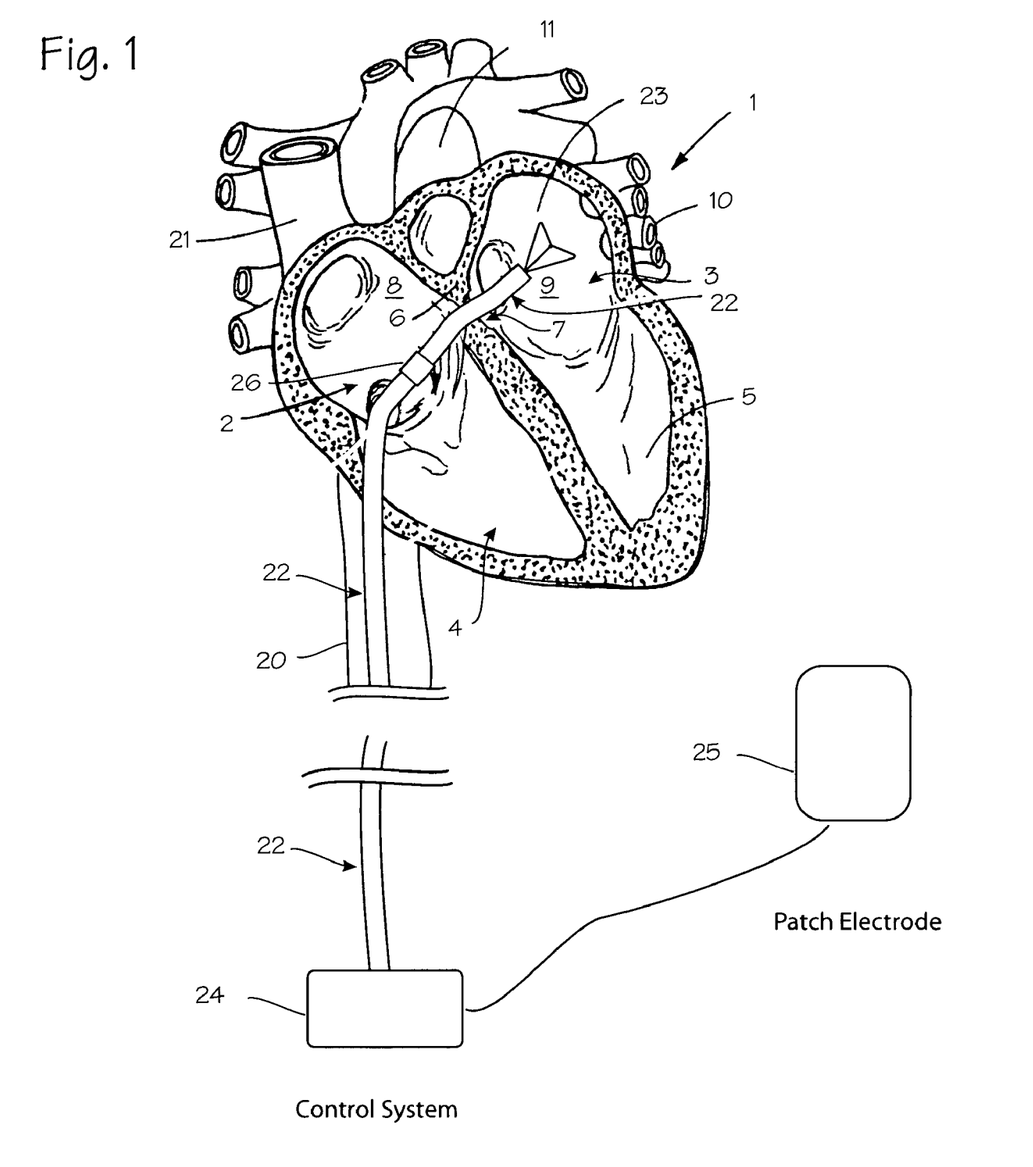
FIG. 1 illustrates the treatment to be accomplished with the devices and methods described below.

FIG. 1 illustrates the treatment to be accomplished with the devices and methods described below. FIG. 1 shows a cutaway view of the human heart 1, showing the major structures of the heart including the right atrium 2, the left atrium 3, the right ventricle 4, and the left ventricle 5. The atrial septum 6 separates the left and right atria. The fossa ovalis 7 is a small depression in the atrial septum which is easily punctured and easily heals, and may be used as an access pathway to the left atrium from the right atrium. In a patient suffering from atrial fibrillation, aberrant electrically conductive tissue may be found in the atrial walls 8 and 9, as well as in the pulmonary veins 10 and pulmonary arteries 11. Ablation of these areas, referred to as arrhythmogenic foci (and also referred to as drivers or rotors), is an effective treatment for atrial fibrillation. Though circumferential ablation of the pulmonary veins cures the arrhythmia which originates in the pulmonary veins, it often results in rapid stenosis of the pulmonary veins. Ablation of foci, rotors or drivers on atrial walls, however, may prevent the propagation of any aberrant electrical activity that originates in the pulmonary veins.

To accomplish this, a catheter is inserted into the atrium, preferably through the inferior vena cava 20, as shown in the illustration, or through the superior vena cava 21, into the right atrium or left atrium. When passing into the left atrium, as illustrated, the catheter penetrates the fossa ovalis (a transseptal puncture will facilitate the crossing). The catheter 22 carries a distal electrode array 23 into the atrium, and this electrode array is adapted to be pressed into contact with the atrial wall. The electrode array is electrically connected to circuitry in a control system 24 which is operable to analyze electrical signals detected by the electrodes and pass RF current through the electrodes and heart tissue to ablate the tissue. A surface electrode 25 is mounted on the patient's body (typically on the back) to permit use of the electrodes in monopolar modes. A return electrode 26 may also be provided on the catheter 22, proximal to the electrode array 23. Using the catheter, an electrophysiologist will map regions of the atrial walls and apply energy through the catheter to ablate any arrhythmogenic foci which are identified in the mapping procedure. The procedure may be repeated as necessary throughout the atrium.

Figure 2:
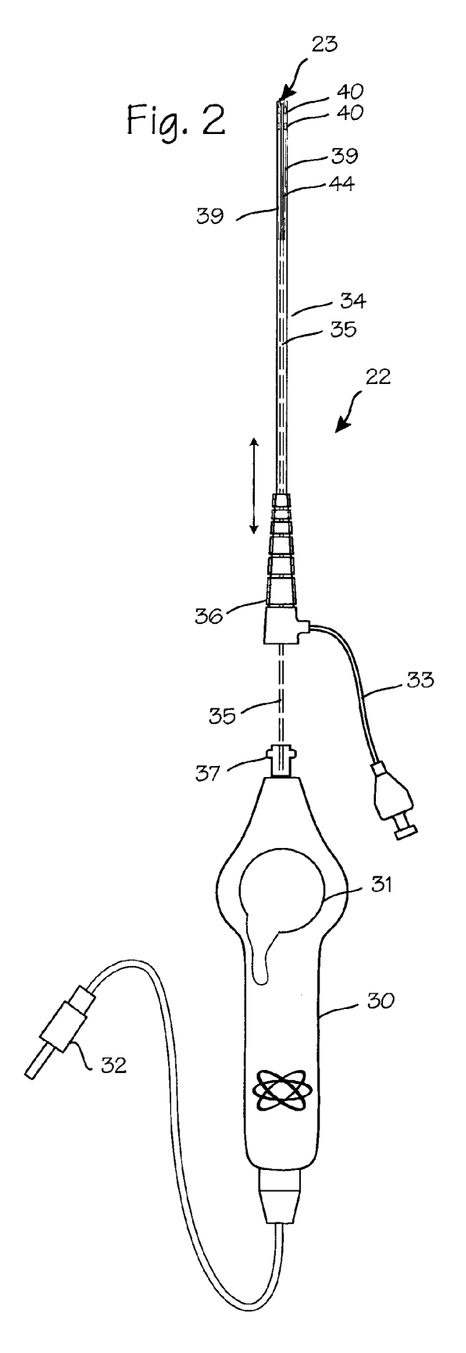
FIG. 2 illustrates an atrial sensing and ablation catheter with an expandable electrode array constrained within an outer catheter tube.

FIG. 2 illustrates an atrial sensing and ablation catheter 22 with an expandable electrode array. The catheter comprises a handle 30 with a steering control knob 31, electrical connector 32 and side-arm connector 33. The electrical connector is used to connect the catheter to the control box. An outer catheter tube 34 is slidably mounted on the inner catheter tube 35, and they may be releasably secured to each other by sliding the proximal portion of the outer catheter sheath strain relief 36 over the cylindrical detent 37 which is fixed to the handle. The side arm connector is used as a flushing port, to allow the flushing of debris and blood from the space between the inner and outer catheter tubes. The electrode array 23 is fixed to the inner catheter tube 35, and is restrained within the distal portion of the outer catheter tube 34.

Figure 3:
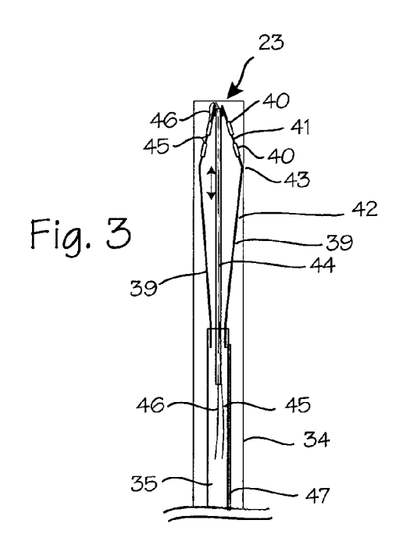
FIG. 3 is an enlarged view of the distal portion of the catheter of FIG. 2.
Figure 5:
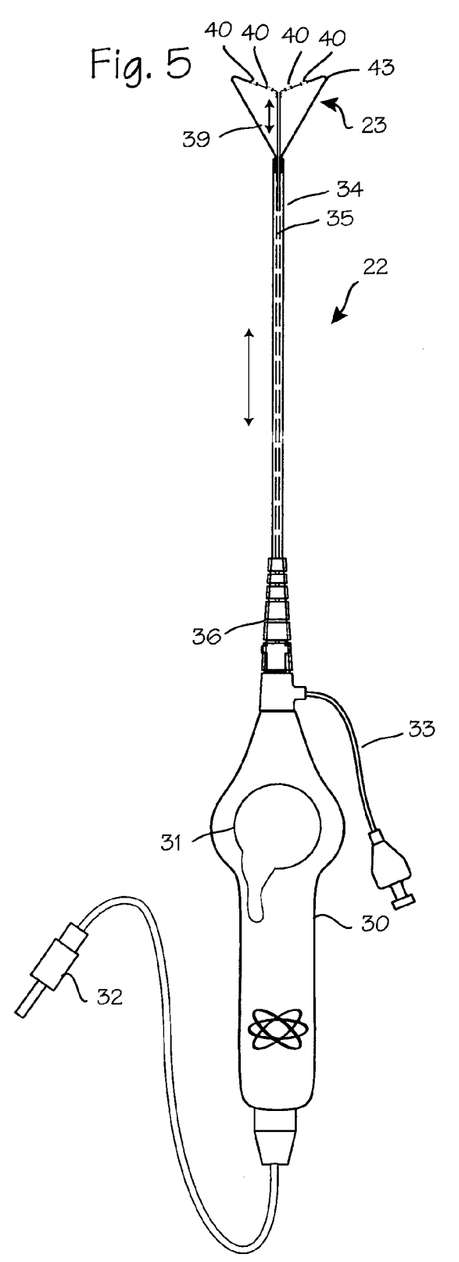
FIG. 5 illustrates the atrial sensing and ablation catheter of FIG. 2 with the electrode array in its expanded configuration.

FIG. 3 is an enlarged view of the distal portion of the catheter of FIG. 2. The electrode array 23 comprises a number of resiliently biased arms 39 which each carry a number of electrodes 40. An array of five arms, each of which carry two electrodes, is suitable for use in the atria. The arms each comprise a wire (preferably a flat wire) with a distal section 41, a proximal section 42 and an intervening bend section 43. The electrodes are placed on the distal sections. The proximal end of each arm is fixed to the inner catheter tube 35. The distal end of each arm is fixed to the floating tube (or pin) 44. This floating tube is retained within the inner catheter tube, but is free to slide longitudinally within the inner catheter tube. The necessary electrical wires 45 and 46 which connect the electrodes to the control system run from each electrode proximally along the arm (and through any intervening electrodes), and enter the lumen of the floating tube 44 and then run proximally through the inner catheter tube and into the catheter handle. (Additional wires for temperature sensing thermistor or thermocouples may be included.) The wires are looped within the handle to provide the distension necessary for the resilient deployment of the electrode array as illustrated in FIG. 5. A steering pull wire 47 is secured to the distal end of the inner catheter tube. The pull wire runs proximally to the steering control knob in the proximal handle, and is operably connected to the control knob so that rotation of the control knob pulls the pull wire to effectuate steering of the distal end of the device. The outer catheter tube is sufficiently flexible so that it is steered by deflection of the inner catheter tube. The materials used for each component are selected to provide the suitable flexibility, column strength and steerability. The outer catheter tube 34 may comprises nylon, polyester or other suitable polymer, and the inner catheter tube 35 comprises a stainless steel coil covered in shrink tubing to provide tensile strength. The electrode arms 39 comprise flat nitinol wires. The floating tube 44 comprises a stainless steel coil. The floating tube may be disposed over the inner catheter if accommodations are made for proximal fixation of the proximal arm segments to the inner catheter, such as placing the fixation points proximally on the inner catheter or providing slots on the proximal portion of the floating tube. The electrode wires may be disposed on or in the wall of the inner catheter, rather than passing through the lumen of the inner catheter as shown in the Figures.

Figure 4:
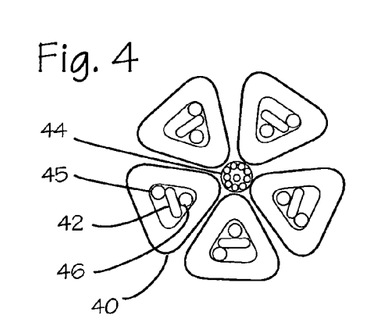
FIG. 4 is a cross-section of the distal portion of the catheter of FIG. 2.
Figure 6:
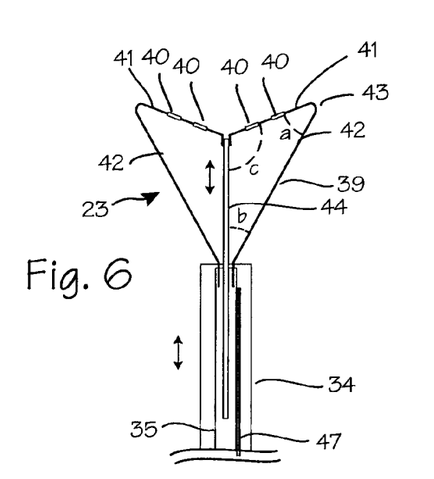
FIG. 6 is an enlarged view of the electrode array in its expanded configuration.

FIG. 4 is a cross-section of the distal portion of the catheter of FIG. 2. At this cross section, an electrode 40 is mounted on each arm 39. These electrodes will be located on the inner portion of the deployed array as shown in FIGS. 5 and 6. The electrodes are tubes of triangular cross section, with tissue contacting faces directed radially outwardly from the catheter. The electrode wires 45, which are connected to the outside electrodes, run through the inside electrodes on their route to the floating tube. The electrode wires 46 are fixed to the inner wall of the inner electrode. As shown in this view, the electrodes are collapsed upon the floating tube 44, and due to the triangular shape they are securely packed within the outer catheter tube 34. The floating tube 44 also houses the various electrode wires 45 and 46.

FIGS. 5 and 6 illustrate the atrial sensing and ablation catheter of FIG. 2 with the electrode array in its expanded configuration. The outer catheter tube 34 has been withdrawn proximally over the catheter inner tube, allowing the array arms 39 to expand to create substantially triangular array segments. Each proximal arm segment resiliently bends radially outwardly from the proximal connection with the inner catheter tube, while each distal arm segment bends radially inwardly from the bend portion toward the longitudinally axis of the catheter. Preferably, the distal arm segments also tend proximally, and establish an acute angle a with the proximal arm segment from which it extends, and the angle is small such that the distal end of the distal arm segment (the point of attachment to the floating tube) is proximal to the bend point. The angle b, which is the angle between the long axis of the catheter and the proximal arm segment, is also an acute angle. The angle c between the catheter longitudinal axis and the distal arm segment is thus obtuse, creating a forward biased array. Generally, the forward biased array results from providing a bend angle a which is less than 90−b, or, conversely, providing a bend angle a such that a+b is less than 90°. In embodiments where the arm segments are not straight, the overall curvature of the arms may provide an arc such that the angle b is acute and the angle c is obtuse.

The resilient expansion of the electrode array pushes the floating tube 44 proximally into the inner catheter tube. When the outer catheter tube is pushed distally over the electrode array, the distal electrode arms will be forced distally, as the proximal segments are compressed inwardly starting from the proximal end, to first splay the distal segments toward and through a perpendicular relationship with the floating tube such that the joint between the arms and the floating tube is distal to the bend point, while drawing the floating tube distally within the inner catheter tube.

Figure 7:
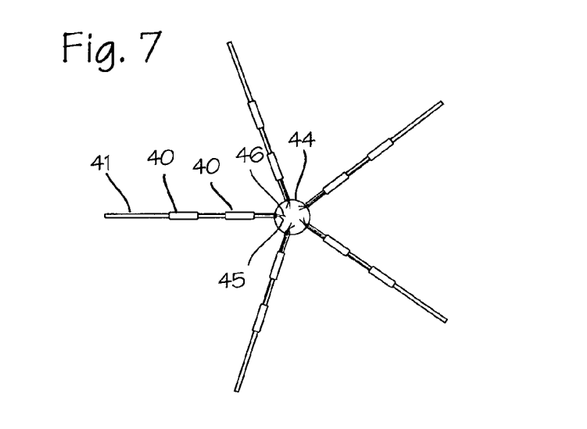
FIG. 7 is an end view of the electrode array in its expanded configuration.

FIG. 7 is an end view of the electrode array in its expanded configuration. In this view, the five arm array is fully expanded resiliently and resiliently flattened as if pressed against a flat surface, to create a substantially planar arrangement of the distal arm segments and the electrodes. The array provides two pairs of electrodes on each of five arms evenly distributed about the floating tube 44. The electrode wires 45 and 46 can be seen extending inwardly from the electrodes and running proximally down the floating tube. The arms are each separated from the adjacent arms by about 72°, for form a pentagram (the actual shape obtained within the heart will of course diverge from the ideal due to resilient deformation as the array is pressed against the atrium walls). The array, when deployed and flattened as shown, is preferably about 15 to 30 mm in diameter (to the outer extent of the arm), with each distal arm segment 41 being about 7.5 to 15 mm long. The diameter of the electrode group (from the center to the outer extent of the electrodes) is preferably about 2 to 30 mm. The wire width is preferable about 0.26 mm, and the distal face of the electrodes is preferably about 1 to 2 mm wide and 2 to 3 mm long (the illustrated electrodes are 2 mm wide and 1.6 mm wide). The electrode array can comprise any number of arms, and each arm can carry any number of electrodes, though the five arm array, with dimensions described above, is well suited for the typical atrial ablation therapy.

Figure 8:
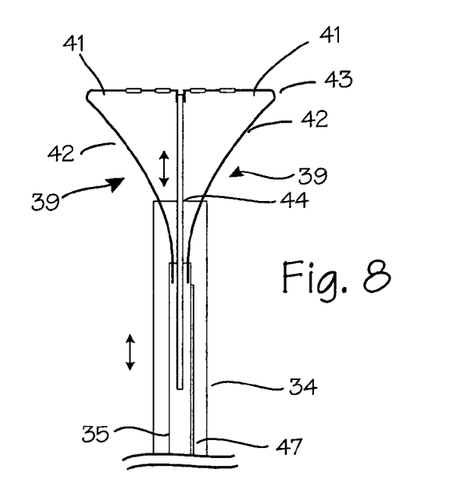
FIGS. 8 and 9 illustrate the mechanism of recapture of the electrode array of the atrial ablation catheter.
Figure 9:
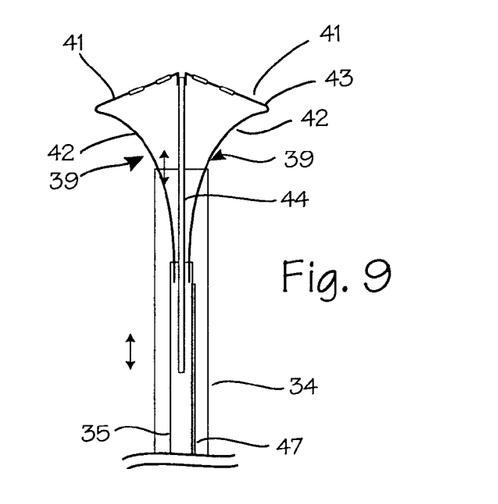

FIGS. 8 and 9 illustrate the mechanism of recapture of the electrode array. When the outer catheter tube 34 is pushed distally over the inner catheter tube 35 and the electrode array, the distal electrode arms 41 will be forced distally, as the proximal segments 42 are compressed inwardly starting from the proximal end, as shown in FIG. 8. This initially splays the distal segments toward a perpendicular relationship with the floating tube as shown in FIG. 8. As the outer catheter tube is translated further distally, such that the joint between the arms and the floating tube is distal to the bend point, the distal arm segments become further splayed, such that they are distal to the proximal arms segments. Because the distal arm segments are fixed to the floating tube, their movement distally draws the floating tube distally within the inner catheter tube. The array is completely captured when the outer catheter tube is translated fully forward to resume the position shown in FIGS. 2 and 3. As can be seen from the illustration, the bend sections provide a means for rotatably joining the distal arm segment to the proximal arm segment, and other suitable mechanisms, such as hinges, may be used instead.

Figures 10, 11:
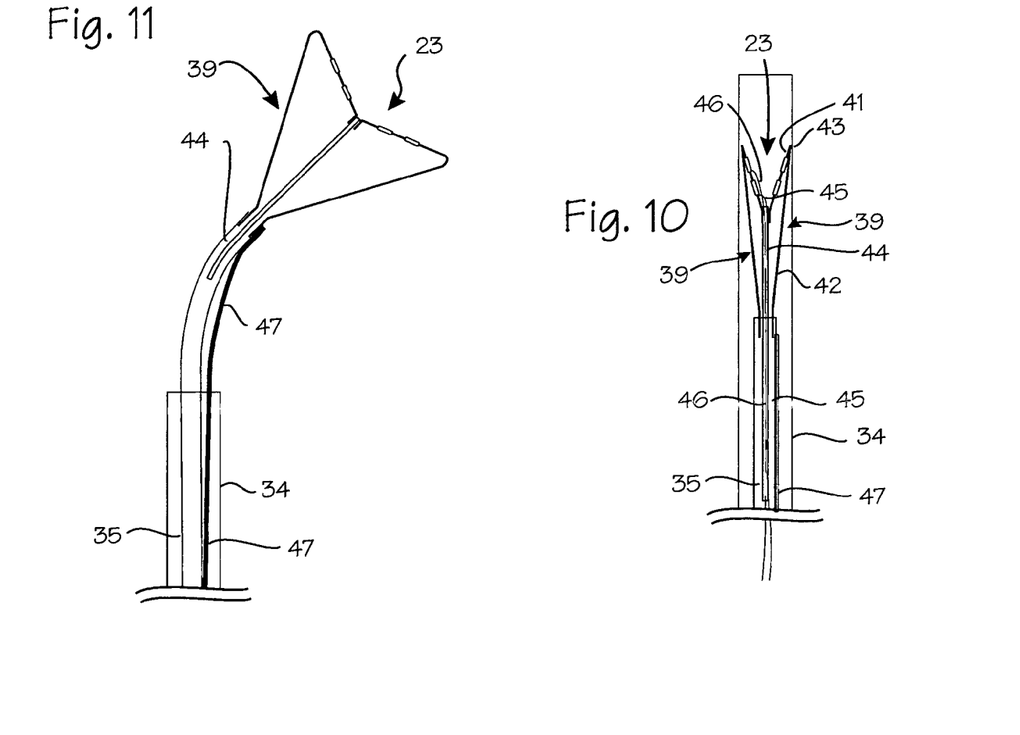
FIG. 10 illustrates an alternate mechanism of recapture of the electrode array of the atrial ablation catheter.
FIG. 11 illustrates the operation of the steering system of the atrial ablation catheter.

FIG. 10 illustrate an alternate mechanism of recapture of the electrode array of the atrial ablation catheter. In the device shown in FIG. 10, the small diameter configuration is achieved by folding the distal arm segments axially inside the proximal arm segments. This is achieved by biasing the proximal arm segments to bow outwardly, providing an inward component of force when compressed by action of the outer catheter tube. Recapture of the array after use may be aided by pulling proximally on the floating tube with a control wire operable from the proximal handle.

FIG. 11 illustrates the operation of the steering system of the atrial ablation catheter. The steering pull wire 47 is secured to the distal end of the inner catheter tube 35, such that pulling the pull wire proximally deflects the distal end of the inner catheter tube. Using the pull wire, the operator can steer the array as needed to contact different areas of the atrium wall. The pull wire may, as shown, be unsecured to the inner catheter tube along much of its length, or it may be embedded in the inner catheter tube wall or otherwise restrained to the inner catheter tube. The entire distal end of the catheter may also be steered with this pull wire, as the outer catheter tube is sufficiently flexible that it will deform along with the inner catheter tube. If desired, similar steering can be effected with a pushable wire or stylet in place of the pull wire.

Figures 12, 13:
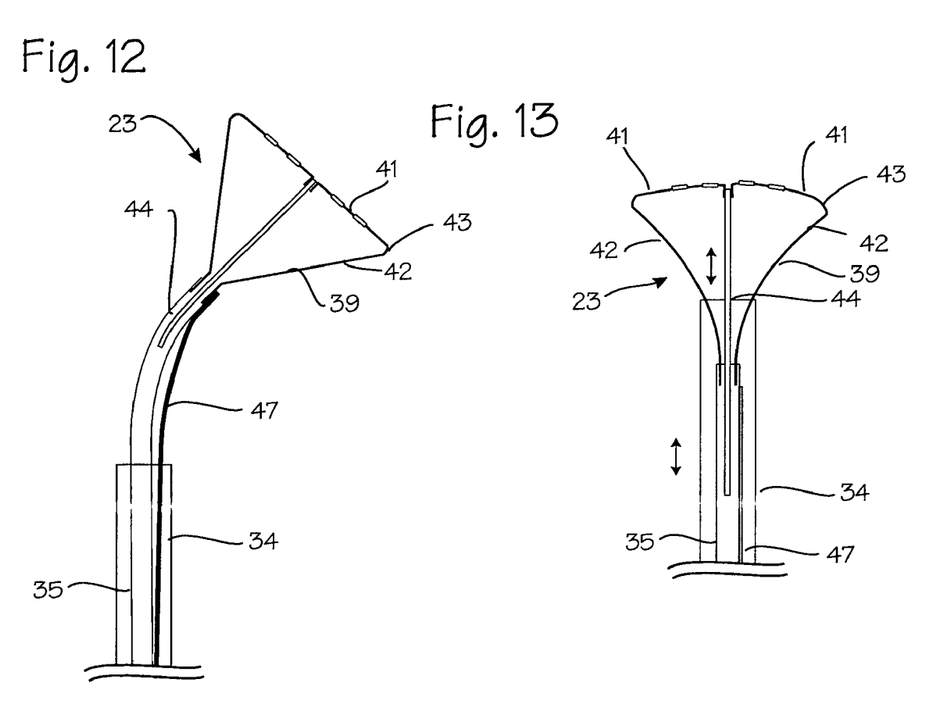
FIG. 12 illustrates the electrode array in the configuration it takes on when pressed against a surface.
FIG. 13 illustrates the electrode array in the configuration it takes on when pressed against a concave surface such as the atrial wall.

FIG. 12 illustrates the electrode array in the configuration it takes on when pressed against the atrial wall. After the array has been steered to face a target site within the atrium, the operator will press the distal face of the array into contact with the atrium wall, and this may cause the distal face to deform, resiliently, to a substantially flat configuration as shown. Given the concave curvature of the atrium chamber, the array will deform to obtain distal arm segments with slightly convex curvature as shown in FIG. 12.

Figure 14:
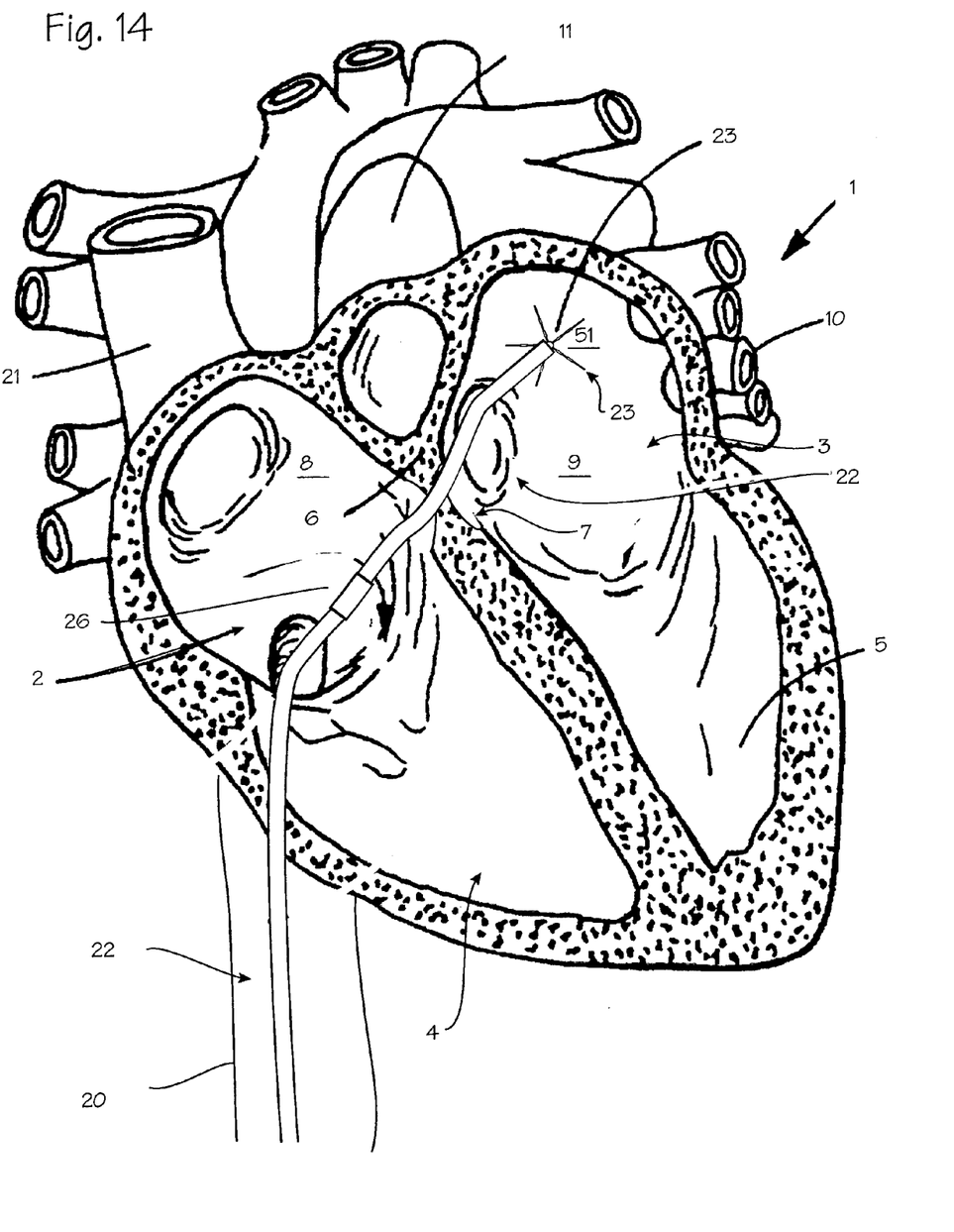
FIG. 14 illustrates a method for using the electrode array in a monopolar mode.

After contact has been established between the atrium wall and the electrode array, the operator will analyze electrical signals detected by the electrodes to determine if the array has been placed over an arrhythmogenic focus. If it has, the operator may energize any of the electrodes, as appropriate, to ablate the focus. Bipolar RF energy may be applied between pairs of the electrodes, or monopolar energy may be applied to any of the electrodes (grounded to the surface electrode or a return electrode located proximally on the catheter body). FIG. 14 illustrates a method for using the electrode array in a monopolar mode, especially in sensitive areas of the atrium such as the back wall (the posterior wall) and the ostia of the pulmonary veins. As shown, the electrode array is placed over the posterior wall 51 of the left atrium, with electrodes in contact with the atrium wall. This wall is fairly thin, and the patient's esophagus lies immediately behind this wall. Ablation in this area entails a risk of perforating the atrial wall and the esophagus. To reduce this risk, the electrode array is operated in a monopolar mode. For each arrhythmogenic focus found by the electrophysiologist (based on the electrical signals detected by the various electrodes), an appropriate electrode can be energized in a monopolar mode to direct ablative RF power to the atrial wall, while the return electrode 26 provides a ground for the RF energy. With the return electrode on the catheter, the current densities around the electrode will be sufficient to locally ablate the atrial wall, but because the RF energy takes a path toward the return electrode, the current density at the epicardial surface of the atrium, and in surrounding structures such as the esophagus, will be minimized. The device may be used is this mode to ablate the ostium of a pulmonary vein, and treatment of the ostium may include additional steps of ablating the ostium with the electrode in a first orientation, then rotating the electrode array and maintaining (or re-establishing) contact with the ostium to establish contact in a second orientation and then ablating the ostium with the electrode in the second orientation, and repeating as necessary to create a ring of ablated zones establishing substantially circumferential ablation of the pulmonary vein ostium.

Though the ablation device has been described in terms of its preferred endocardial and transcutaneous method of use, the array may be used on the heart during open heart surgery, open chest surgery, or minimally invasive thoracic surgery. Thus, during open chest surgery, a short catheter or cannula carrying the electrode array may be inserted into the heart through the wall of the right atrium or through the vena cava, or an electrode array may be applied directly to the atrium wall through an incision in the left atrium wall. Also, the electrode array may be applied to the epicardial surface of the atrium or other areas of the heart to detect and ablate arrhythmogenic foci from outside the heart.

While the preferred embodiments of the devices and methods have been described in reference to the environment in which they were developed, they are merely illustrative of the principles of the inventions. Other embodiments and configurations may be devised without departing from the spirit of the inventions and the scope of the appended claims.

We claim:

1. An ablation catheter, comprising:
   a catheter having a longitudinal axis and further having a proximal end and a distal end;
   an electrode array disposed on the distal end of the catheter, said electrode array comprising a plurality of resilient arms, each arm having a proximal arm segment and a distal arm segment resiliently or rotatably joined to each other at a bend point, whereby the electrode array may be retained in a small diameter configuration within the catheter and released to assume a large diameter configuration, wherein the large diameter configuration comprises the proximal arm segments bent radially outwardly from the catheter with the distal arm segments extending radially inwardly from the proximal arm segments, wherein in the large diameter configuration, the proximal arm segments are configured such that the same may transmit forces substantially along the longitudinal axis, such that the catheter may be controllably pushed in a distal direction to contact tissue; and
   at least one electrode disposed on each of the distal arm segments of the array, and
   wherein, in the small diameter configuration, the distal arm segments are restrained within a segment of an outer catheter tube which is distal to the proximal arm segments, and extend distally from the bend point.

2. An ablation catheter, comprising:
   a catheter having a longitudinal axis and further having a proximal end and a distal end;
   an electrode array disposed on the distal end of the catheter, said electrode array comprising a plurality of resilient arms, each arm having a proximal arm segment and a distal arm segment resiliently or rotatably joined to each other at a bend point, whereby the electrode array may be retained in a small diameter configuration within the catheter and released to assume a large diameter configuration wherein the large diameter configuration comprises the proximal arm segments bent radially outwardly from the catheter with the distal arm segments extending radially inwardly from the proximal arm segments, wherein in the large diameter configuration, the proximal arm segments are configured such that the same may transmit forces substantially along the longitudinal axis, such that the catheter may be controllably pushed in a distal direction to contact tissue; and at least one electrode disposed on each of the distal arm segments of the array, wherein the distal arm segments tend distally from the bend point in the large diameter configuration and tend distally from the bend point in the small diameter configuration.

3. An ablation catheter, comprising:

a catheter having a longitudinal axis and further having a proximal end and a distal end;

an electrode array disposed on the distal end of the catheter, said electrode array comprising a plurality of resilient arms, each arm having a proximal arm segment and a distal arm segment resiliently or rotatably joined to each other at a bend point, whereby the electrode array may be retained in a small diameter configuration within the catheter and released to assume a large diameter configuration, wherein the large diameter configuration comprises the proximal arm segments bent radially outwardly from the catheter with the distal arm segments extending radially inwardly from the proximal arm segments; and at least one electrode having a non-circular cross-section disposed on each of the distal arm segments of the array and, wherein the distal arm segments tend distally from the bend point in the large diameter configuration and tend distally from the bend point in the small diameter configuration.

4. An ablation catheter, comprising:

a catheter having a longitudinal axis and further having a proximal end and a distal end;

an electrode array disposed on the distal end of the catheter, said electrode array comprising a plurality of resilient arms, each arm having a proximal arm segment and a distal arm segment resiliently or rotatably joined to each other at a bend point, whereby the electrode array may be retained in a small diameter configuration within the catheter and released to assume a large diameter configuration, wherein the large diameter configuration comprises the proximal arm segments bent radially outwardly from the catheter with the distal arm segments extending radially inwardly from the proximal arm segments; and at least one electrode having a non-circular cross-section disposed on each of the distal arm segments of the array and, wherein, in the small diameter configuration, the distal arm segments are restrained within a segment of an outer catheter tube which is distal to the proximal arm segments, and extend distally from the bend point.

5. An ablation catheter, comprising:

a catheter having a longitudinal axis and further having a proximal end and a distal end;

an electrode array disposed on the distal end of the catheter, said electrode array comprising a plurality of resilient arms, each arm having a proximal arm segment and a distal arm segment resiliently or rotatably joined to each other at a bend point, whereby the electrode array may be retained in a small diameter configuration within the catheter and released to assume a large diameter configuration, wherein the large diameter configuration comprises the proximal arm segments bent radial outwardly from the catheter with the distal arm segments extending radially inwardly from the proximal arm segments; and at least one electrode disposed on each of the distal arm segments of the array, such that the at least one electrode is configured to receive signals containing information about foci corresponding to atrial fibrillation and is further configured to ablate the foci and, wherein the distal arm segments tend distally from the bend point in the large diameter configuration and tend distally from the bend point in the small diameter configuration.

6. An ablation catheter. comprising:

a catheter having a longitudinal axis and further having a proximal end and a distal end;

an electrode array disposed on the distal end of the catheter, said electrode array comprising a plurality of resilient arms, each arm having a proximal arm segment and a distal arm segment resiliently or rotatably joined to each other at a bend point, whereby the electrode array may be retained in a small diameter configuration within the catheter and released to assume a large diameter configuration, wherein the large diameter configuration comprises the proximal arm segments bent radially outwardly from the catheter with the distal arm segments extending radially inwardly from the proximal arm segments; and at least one electrode disposed on each of the distal arm segments of the array, such that the at least one electrode is configured to receive signals containing information about foci corresponding to atrial fibrillation and is further configured to ablate the foci and, wherein, in the small diameter configuration, the distal arm segments are restrained within a segment of an outer catheter tube which is distal to the proximal arm segments, and extend distally from the bend point.

7. An ablation catheter comprising:

an outer catheter tube;

an inner catheter tube slidably disposed within the outer catheter tube, said inner catheter tube having a distal end adapted for insertion into a vessel of the body;

a floating tube slidably disposed relative to the inner catheter tube, the floating tube having a length substantially less than that of the outer catheter tube and inner catheter tube; and an electrode array comprising a plurality of resilient arms, each arm having a proximal arm segment fixed to the inner catheter tube and a distal arm segment fixed to the floating tube, whereby the electrode array may be compressed by longitudinal translation of the outer catheter tube relative to the inner catheter tube, and the floating tube longitudinally translates relative to the inner tube to accommodate longitudinal movement of the distal end of the resilient arms in response to compression of the electrode array;

a plurality of electrodes disposed on each of the distal arm segments of the array.

8. The ablation catheter of claim 7, wherein:

the floating tube is disposed at least partially within the distal end of the inner catheter tube.

9. The ablation catheter of claim 7, wherein:
the electrode array is resiliently movable from a small diameter configuration to a large diameter configuration, and in the large diameter configuration each proximal arm segment resiliently bends radially outwardly from the inner catheter tube, and each distal arm segment bends radially inwardly toward the longitudinal axis of the catheter from a bend point connecting the proximal arm segment to the distal arm segment, creating an acute angle between each distal arm segment and its associated proximal arm segment.

10. The ablation catheter of claim 7, wherein:
the electrode array is resiliently movable from a small diameter configuration and a large diameter configuration, and in the large diameter configuration each proximal arm segment resiliently bends radially outwardly from the inner catheter tube, and each distal arm segment bends radially inwardly and proximally toward the longitudinal axis of the catheter from a bend point connecting the proximal arm segment to the distal arm segment.

11. The ablation catheter of claim 7, wherein:
the electrode array is resiliently movable from a small diameter configuration and a large diameter configuration, and in the large diameter configuration each proximal arm segment resiliently bends radially outwardly from the inner catheter tube, and each distal arm segment bends radially inwardly and proximally toward the longitudinal axis of the catheter from a bend point connecting the proximal arm segment to the distal arm segment, and said electrode arms are further deformable upon pressing the array against a surface to position the distal arm segments into a substantially planar arrangement.

12. The ablation catheter of claim 9, 10 or 11 wherein, in the small diameter configuration, the distal arm segments are restrained within a segment of the outer catheter tube which is distal to the proximal arm segments, and extend distally from the bend point.

13. The ablation catheter of claim 9, 10 or 11 wherein, in the small diameter configuration, the distal arm segments are folded inwardly so as to be disposed proximate the proximal arm segments and extend proximally from the bend point.

14. The ablation catheter of claim 11, further comprising a control wire fixed to the floating tube and operable from the proximal end of the catheter to pull the floating tube proximally.

15. The ablation catheter of claim 7, wherein:
the floating tube comprises a stainless steel coil.

16. An ablation catheter comprising:
a catheter having a longitudinal axis and further having a proximal end and a distal end;
an electrode array disposed on the distal end of the catheter, said electrode array comprising a plurality of resilient arms, each arm having a proximal arm segment and a distal arm segment resiliently or rotatably joined to each other at a bend point, whereby the electrode array may be retained in a small diameter configuration within the catheter and released to assume a large diameter configuration, wherein the large diameter configuration comprises the proximal arm segments bent radially outwardly from the catheter with the distal arm segments extending radially inwardly from the proximal arm segments;
such that in the large diameter configuration the distal arm segments are configured to be substantially perpendicular to the longitudinal axis of the catheter when the catheter is pushed in a distal direction to contact an area of tissue to be ablated; and
at least one electrode disposed on each of the distal arm segments of the array, and
wherein the distal arm segments tend proximally from the bend point in the large diameter configuration and tend distally from the bend point in the small diameter configuration, and
wherein, in the small diameter configuration, the distal arm segments are folded inwardly so as to be disposed proximate the proximal arm segments and extend proximally from the bend point.

17. An ablation catheter comprising:
a catheter having longitudinal axis and further having a proximal end and a distal end;
an electrode array disposed on the distal end of the catheter, said electrode array comprising a plurality of resilient arms, each arm having a proximal arm segment and a distal arm segment resiliently or rotatably joined to each other at a bend point, whereby the electrode array may be retained in a small diameter configuration within the catheter and released to assume a large diameter configuration, wherein the large diameter configuration comprises the proximal arm segments bent radially outwardly from the catheter with the distal arm segments extending radially inwardly from the proximal arm segments;
such that in the large diameter configuration the distal arm segments are configured to be substantially perpendicular to the longitudinal axis of the catheter when the catheter is pushed in a distal direction to contact an area of tissue to be ablated; and
at least one electrode disposed on each of the distal arm segments of the array, and
wherein the distal arm segments tend proximally from the bend point in the large diameter configuration and tend distally from the bend point in the small diameter configuration, and
wherein, in the small diameter configuration, the distal arm segments are folded inwardly so as to be disposed proximate the proximal arm segments and extend proximally from the bend point, and
further comprising a control wire fixed to a floating tube and operable from the proximal end of the catheter to pull the floating tube proximally.

18. A method of treating atrial fibrillation comprising:
providing a catheter comprising:
an outer catheter tube;
an inner catheter tube slidably disposed within the outer catheter tube, said inner catheter tube having a distal end adapted for insertion into a vessel of the body;
a floating tube slidably disposed relative to the inner catheter tube, the floating tube having a length substantially less than that of the outer catheter tube and inner catheter tube; and
providing an electrode array comprising:
a plurality of resilient arms, each arm having a proximal arm segment and a distal arm segment connected by a bend point, said arms being resiliently biased to bend at an acute angle at the bend points, and a plurality of electrodes disposed on each of the distal arm segments;
fixing the proximal arm segments to the inner catheter tube;
fixing the distal arm segments to the floating tube;

restraining the electrode array in a small diameter configuration within the outer catheter tube;

inserting the electrode array into the left atrium of the heart of a patient;

withdrawing the outer tube from the electrode array, and allowing the electrode array to resiliently expand so that each proximal arm segment resiliently bends radially outwardly from the inner catheter tube, and each distal arm segment bends radially inwardly and proximally toward the longitudinal axis of the catheter from the bend point;

pressing the electrode array against an area of the heart wall to deform the distal arm segments and contact the electrodes with the heart wall;

sensing electrical signals of the heart wall through the electrodes of the electrode array;

upon determining that the array is disposed over an arrhythmogenic focus in the left atrium, passing energy through the electrode array to ablate a portion of the heart wall;

moving the electrode array as desired to additional areas of the heart wall and repeating the sensing and ablating steps as desired to treat atrial fibrillation.

19. The method of claim 18, further comprising the steps of:

providing a return electrode on the catheter, proximal to the electrodes of the electrode array;

pressing the electrode array against the posterior wall of the left atrium of the heart to sense electrical signals;

operating at least one electrode of the array in monopolar mode in conjunction with the return electrode to ablate a portion of the posterior wall of the left atrium.

20. The method of claim 18, further comprising the steps of:

providing a return electrode an the catheter, proximal to the electrodes of the electrode array;

pressing the electrode array against an ostium of a pulmonary vein opening to the left atrium of the heart to sense electrical signals;

operating at least one electrode of the array in monopolar mode in conjunction with the return electrode to ablate a portion of the left atrium wall surrounding a pulmonary vein.

21. A method of forming an electrode array comprising;

providing a catheter comprising:

an outer catheter tube;

an inner catheter tube slidably disposed within the outer catheter tube, said inner catheter tube having a distal end adapted for insertion into a vessel of the body;

a floating tube slidably disposed relative to the inner catheter tube, the floating tube having a length substantially less than that of the outer catheter tube and inner catheter tube; and providing an electrode array comprising:

a plurality of resilient arms, each arm having a proximal arm segment and a distal arm segment connected by a bend point, said arras being resiliently biased to bend at an acute angle at the bend points, and a plurality of electrodes disposed on each of the distal arm segments;

fixing the proximal arm segments to the inner catheter tube;

fixing the distal arm segments to the floating tube;

restraining the electrode array in a small diameter configuration within the outer catheter tube;

withdrawing the outer tube from the electrode array, and allowing the electrode array to resiliently expand so that each proximal arm segment resiliently bends radially outwardly from the inner catheter tube, and each distal arm segment bends radially inwardly and proximally toward the longitudinal axis of the catheter from the bend point;

pressing the electrode may against a surface to deform the distal arm segments into a substantially planar arrangement.

\* \* \* \* \*

UNITED STATES PATENT AND TRADEMARK OFFICE
CERTIFICATE OF CORRECTION

PATENT NO. : 7,429,261 B2
APPLICATION NO. : 10/997172
DATED : September 30, 2008
INVENTOR(S) : Kunis et al.

It is certified that error appears in the above-identified patent and that said Letters Patent is hereby corrected as shown below:

Col. 8, line(s) 17, delete "diameter, configuration" and insert in place thereof --diameter configuration--.

Col. 10, line(s) 1, delete "longitudina1 axis" and insert in place thereof --longitudinal axis--.

Signed and Sealed this

Eighteenth Day of August, 2009

David J. Kappos
*Director of the United States Patent and Trademark Office*